United States Patent
Tsai et al.

(10) Patent No.: US 12,201,669 B2
(45) Date of Patent: Jan. 21, 2025

(54) SMALL MOLECULE SUPPRESSORS OF APOE GENE EXPRESSION AND CEREBRAL VASCULAR AMYLOID PATHOLOGY

(71) Applicant: Massachusetts Institute of Technology, Cambridge, MA (US)

(72) Inventors: Li-Huei Tsai, Cambridge, MA (US); Joel Blanchard, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/692,821

(22) Filed: Mar. 11, 2022

(65) Prior Publication Data

US 2022/0288157 A1 Sep. 15, 2022

Related U.S. Application Data

(60) Provisional application No. 63/159,847, filed on Mar. 11, 2021.

(51) Int. Cl.
*A61K 38/13* (2006.01)
*A61K 31/436* (2006.01)
*A61P 25/28* (2006.01)

(52) U.S. Cl.
CPC .......... *A61K 38/13* (2013.01); *A61K 31/436* (2013.01); *A61P 25/28* (2018.01)

(58) Field of Classification Search
CPC ........ A61K 38/13; A61K 31/436; A61P 25/28
See application file for complete search history.

(56) References Cited

U.S. PATENT DOCUMENTS 6,316,405 B1 11/2001 Rich et al.
2014/0316104 A1 10/2014 Fischer et al.

FOREIGN PATENT DOCUMENTS

WO WO 2020/154374 A1 7/2020
WO 2020/163594 A1 8/2020

OTHER PUBLICATIONS

Kazmi et al (Scientific Reports, 2018, 8, 17283, 1-13) (Year: 2018).*
Stewart et al (Calcif Tissue Int., Oct. 1989, 45(4), 222-6) (Year: 1989).*
Mamun et al (Oxidative Medicine and Cellular Longevity, vol. 2020, Article ID 5086250, pp. 1-16) (Year: 2020).*
PubChem Document (2005) (Year: 2005).*
Hudry et al (The Journal of Neuroscience, 2012, 32(9), 3176-3192) (Year: 2012).*
PCT/US2022/020018, Apr. 27, 2022, Invitation to Pay Additional Fees.
PCT/US2022/020018, Jun. 29, 2022, International Search Report and Written Opinion.
Invitation to Pay Additional Fees for PCT/US2022/020018 mailed Apr. 27, 2022.
Berge et al., Pharmaceutical Salts. J Pharm Sci. Jan. 1977;68(1):1-19.
International Search Report and Written Opinion mailed Jun. 29, 2022, for Application No. PCT/US2022/020018.
[No Author Listed], PubChem Database Printout for SID 439048060. SCHEMBL22338251. Last modified Dec. 19, 2020. Retrieved from: <https://pubchem.ncbi.nlm.nih.gov/substance/439048060>. 8 pages.
International Preliminary Report on Patentability mailed Sep. 21, 2023, for Application No. PCT/US2022/020018.

\* cited by examiner

*Primary Examiner* — Sudhakar Katakam
(74) *Attorney, Agent, or Firm* — Wolf, Greenfield & Sacks, P.C.

(57) ABSTRACT

The present disclosure provides methods of inhibiting amyloid synthesis in a subject using small molecule inhibitors. The invention also includes methods of treating disease associated with amyloid synthesis, such as Alzheimer's disease. The small molecule inhibitors disclosed herein are compounds which are non-immunosuppressant cyclosporin including the pharmaceutically acceptable salts thereof.

11 Claims, 6 Drawing Sheets

SMALL MOLECULE SUPPRESSORS OF APOE GENE EXPRESSION AND CEREBRAL VASCULAR AMYLOID PATHOLOGY

RELATED APPLICATIONS

This application claims priority under 35 U.S.C. § 119(e) to U.S. Provisional Patent Application No. 63/159,847 filed Mar. 11, 2021, which is hereby incorporated by reference in its entirety.

GOVERNMENT SUPPORT

This invention was made with government support under UG3 NS115064 awarded by the National Institutes of Health. The government has certain rights in the invention.

BACKGROUND

Alzheimer's disease is a chronic neurodegenerative disease having symptoms most commonly including memory loss, difficulties with language, and cognitive impairment. Despite the present and looming toll on society, we have no effective therapies for AD or related dementias. The complexity of AD pathology presents a major challenge to development of therapeutics. AD pathogenesis proceeds over the course of several decades and arises through diverse genetic etiologies. Our understanding of the mechanisms has largely been limited to the effects of early-onset familial AD (fAD). Despite this growing genetic awareness, the next steps are currently missing. Even for the strongest risk factor for sAD, APOE4, the mechanisms underlying its association with AD or related pathologies is largely unclear. Therefore, there are currently no therapeutic or lifestyle interventions to mitigate genetic and nongenetic risk for developing AD.

SUMMARY

In some aspects, a method for inhibiting amyloid synthesis in a subject is provided and comprises administering to the subject a compound comprising a non-immunosuppressant cyclosporin including the pharmaceutically acceptable salts thereof in an effective amount to inhibit amyloid synthesis in the subject.

In some embodiments, the subject has Alzheimer's disease. In some embodiments, the subject has CAA. In some embodiments, the subject has been diagnosed with Alzheimer's disease. In some embodiments, the method further comprises determining whether a subject has or is at risk of developing amyloid accumulation by identifying the subject as APOE4 positive.

In some embodiments, the compound has the following Formula I:

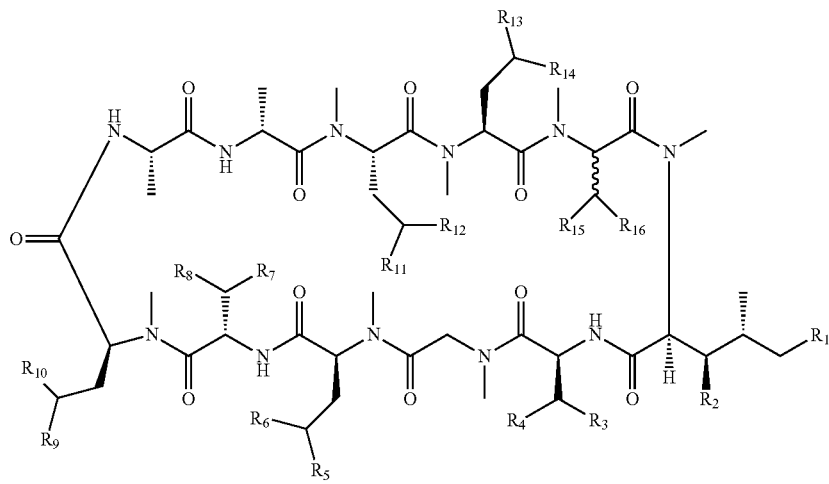

or a pharmaceutically acceptable salt thereof, wherein $R_1$ is —CH=C($R^{1a}$)$_2$ or —CH$_2$C($R^{1a}$)$_3$, wherein each instance of $R^{1a}$ is independently hydrogen, halogen, optionally substituted alkyl, optionally substituted alkenyl, or optionally substituted alkynyl; $R_2$ is —O$R^{2a}$ or —N($R^{2a}$)$_2$, wherein each instance of $R^{2a}$ is independently hydrogen or optionally substituted alkyl; and each of $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ is independently hydrogen, halogen, or optionally substituted alkyl.

In some embodiments, the compound is cyclosporin D

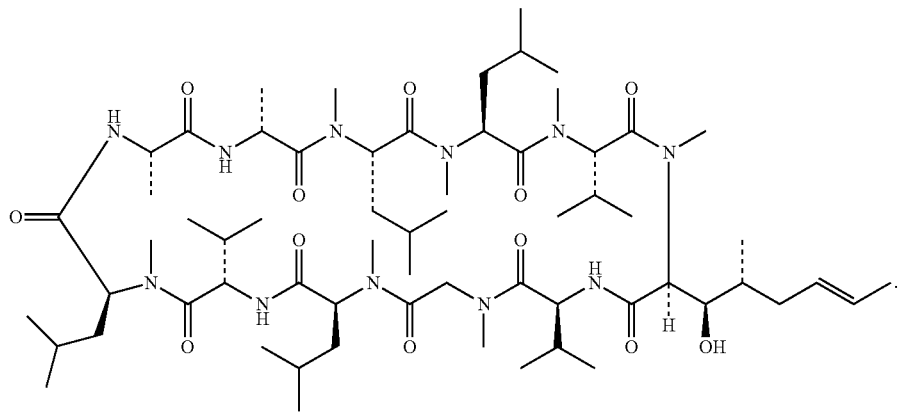 [SMILES: C/C=C/C[C@@H](C)[C@@H](O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

In some embodiments, the compound is cyclosporin H (5-(N-methyl-D-valine)-cyclosporin A)

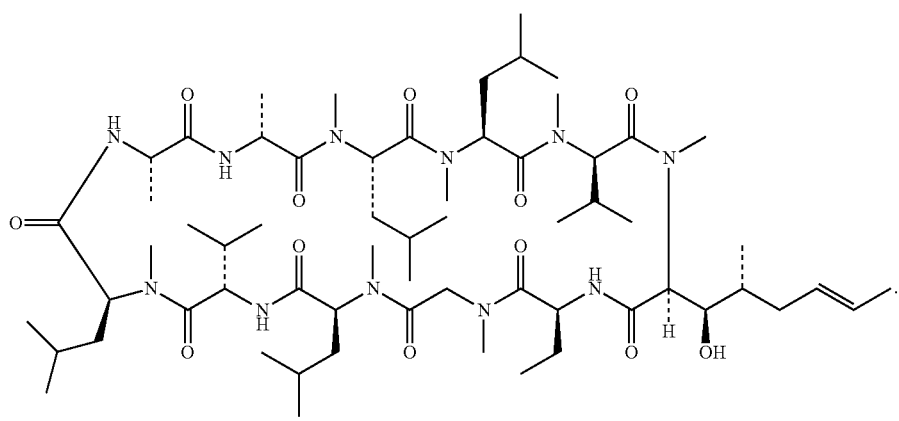 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@H](C(C)C)C(=O)N1C]

In some embodiments, the daily dose administered to the patient is between 1 and 50 mg and the dose is administered once daily. In some embodiments, the method comprises a pharmaceutically acceptable salt that is a hydrochloride.

In some embodiments, the compound is administered as an immediate release formulation. In some embodiments, the compound is administered as a sustained release formulation. In some embodiments, the Alzheimer's disease is mild to moderate Alzheimer's disease. In some embodiments, the Alzheimer's disease is moderate to severe Alzheimer's disease. In some embodiments, the method further comprises administering another therapeutic agent.

In some aspects a method for inhibiting amyloid synthesis in a subject is provided. The method involves administering to the subject a compound comprising a sub-immunosuppressant dose of a calcineurin/NFAT inhibitor including the pharmaceutically acceptable salts thereof in an effective amount to inhibit amyloid synthesis in the subject. In some embodiments the subject has Alzheimer's disease. In some embodiments the subject has CAA. In some embodiments the subject has been diagnosed with Alzheimer's disease. In some embodiments, the method further comprises determining whether a subject has or is at risk of developing amyloid accumulation by identifying the subject as APOE4 positive. In some embodiments the compound is FK506. In some embodiments the compound is cyclosporin A. In some embodiments the compound is administered in an amount that is less than 50% of the daily dose of calcineurin/NFAT inhibitor typically effective in immunosuppression-based therapies or has been previously proposed for treating CAA and Alzheimer's disease or promoting learning and memory when used alone.

The details of one or more embodiments of the invention are set forth in the description below. Other features or advantages of the present invention will be apparent from the following drawings and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION

Figure 1:
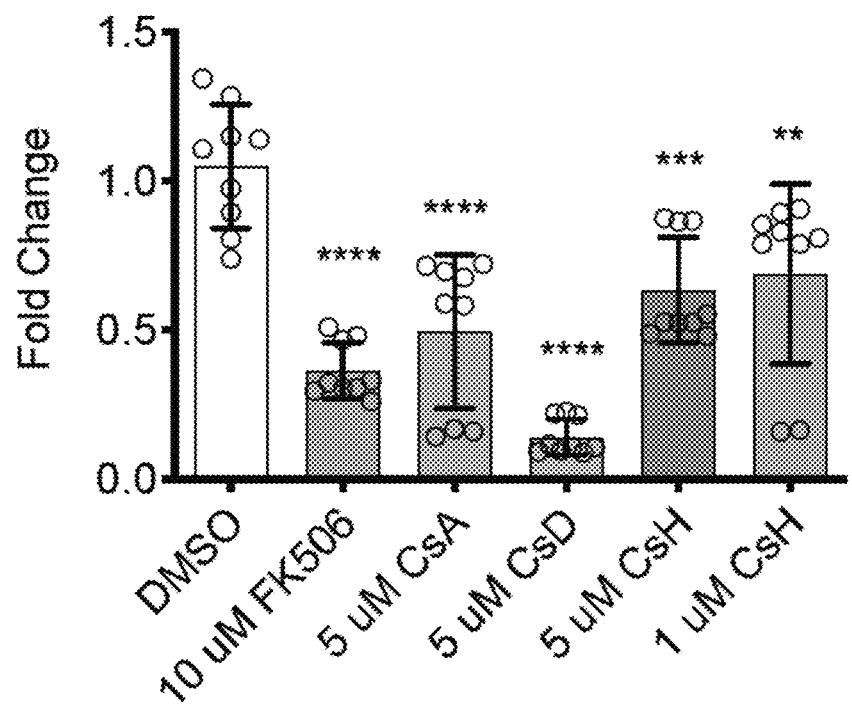
FIG. 1 shows APOE expression after APOE4 pericytes were treated with Cyclosporin analogs for two weeks.
Figure 2A:
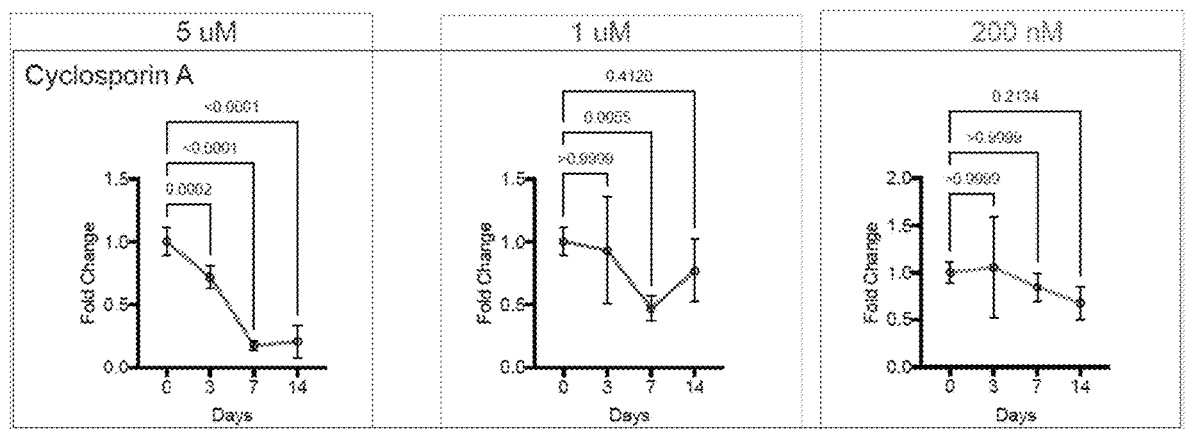
FIGS. 2A-2D show APOE expression measured by qRT-PCR in APOE4/4 pericytes following treatment with Cyclosporin A (FIG. 2A), FK506 (FIG. 2B), Cyclosporin D (FIG. 2C), Cyclosporin H (FIG. 2D). One-way ANOVA with Bonferroni's Multiple Comparison test, 6 replicates per a timepoint.
Figure 2B:
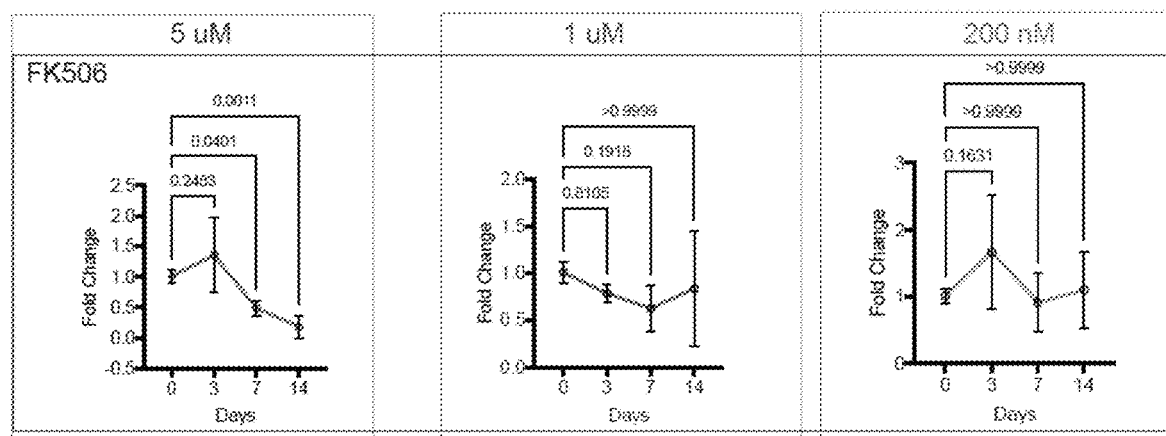
Figure 2C:
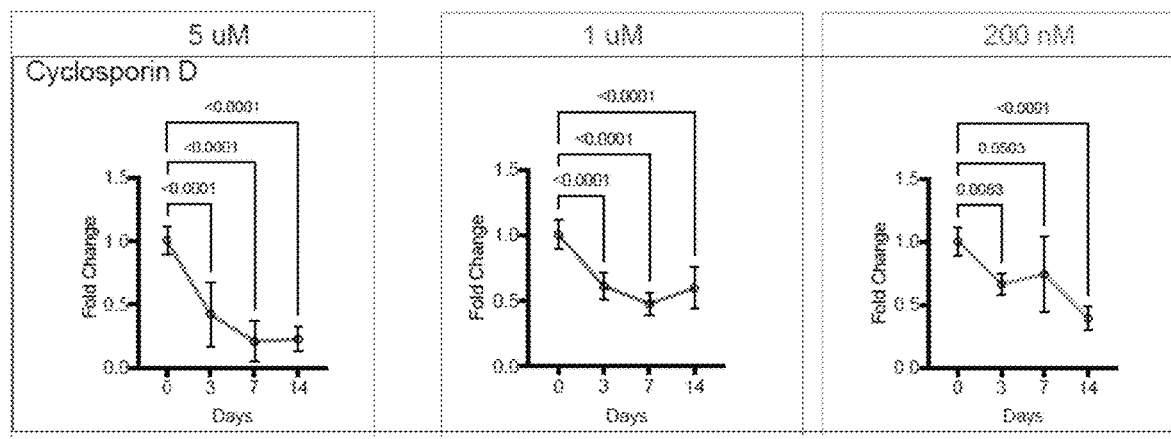
Figure 2D:
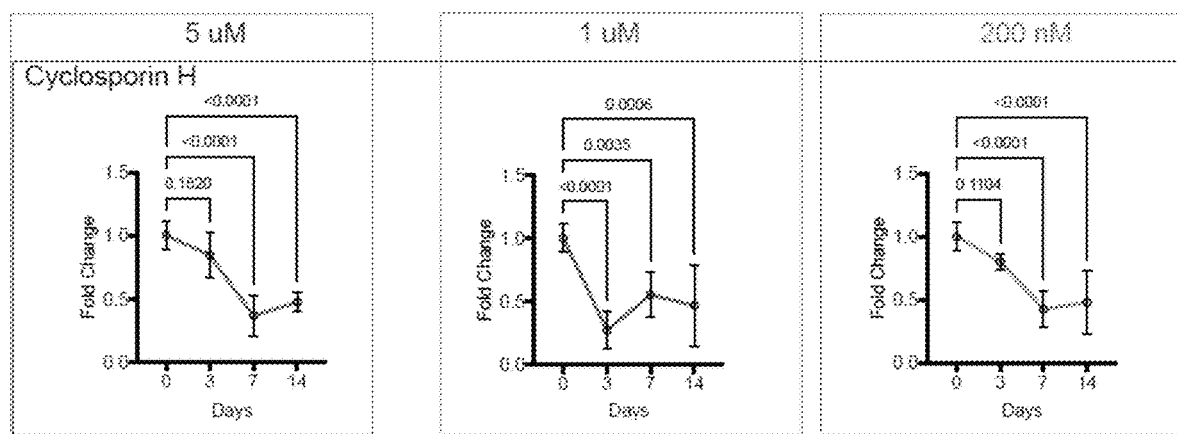

Recent research in the field of Alzheimer's has demonstrated that APOE4 is associated with a leaky blood-brain barrier leading to changes in brain function, and a loss of connections between brain cells. These changes led to high levels of an inflammatory molecule called cyclophilin A (CypA), which could be regulated by APOE2 and APOE3 but not APOE4. Treating animals with immunosuppressant drugs such as cyclosporine A, led to the inhibition of CypA and preserved the integrity of the blood-brain barrier, lessening damage to the brain. It was further shown that transplant patients who took the immunosuppressant cyclosporine after transplant had much lower rates of dementia. Previous studies by the inventors have identified that FK506 and cyclosporin A, both of which have therapeutic activities as immunosuppressants, can reduce the expression of APOE in human pericytes and brain cells and reverse or prevent cerebrovascular pathologies associated with Alzheimer's Disease such as cerebral amyloid angiopathy. These findings suggested that immunosuppressants are desirable for treating amyloid diseases such as Alzheimer's disease.

In contrast to the teachings in the art, it has been discovered herein that small molecules within the cyclosporin family which are devoid of immunosuppressant activity are useful for treating amyloid diseases. It is demonstrated herein that non-immunosuppressant cyclosporins, e.g., cycosporin D and cyclosporin H, are significantly more potent with faster kinetics and able to reduce APOE expression at lower doses than immuosuppressant cyclosporins such as cylcosporin A. Thus, these compounds are useful for the treatment of cerebral amyloid angiopathies, Alzheimer's Disease, and other related diseases and for enhancing learning and memory.

It was also discovered, quite unexpectedly, that therapeutic compounds such as FK506 and cyclosporin A having immunosuppressant activity were capable of modulating the cerebral amyloid phenotype when administered in sub-therapeutic doses which are not sufficient to produce immunosuppressive effects.

In some aspects the invention is a method for inhibiting amyloid synthesis in a subject, by administering to the subject a compound comprising a non-immunosuppressant cyclosporin including the pharmaceutically acceptable salts thereof in an effective amount to inhibit amyloid synthesis in the subject.

A non-immunosuppressant cyclosporin is a cyclosporin which does not cause significant suppression of an immune factor in a subject. Such compounds are known in the art. In some embodiments the non-immunosuppressant cyclosporin is a compound having the following Formula I:

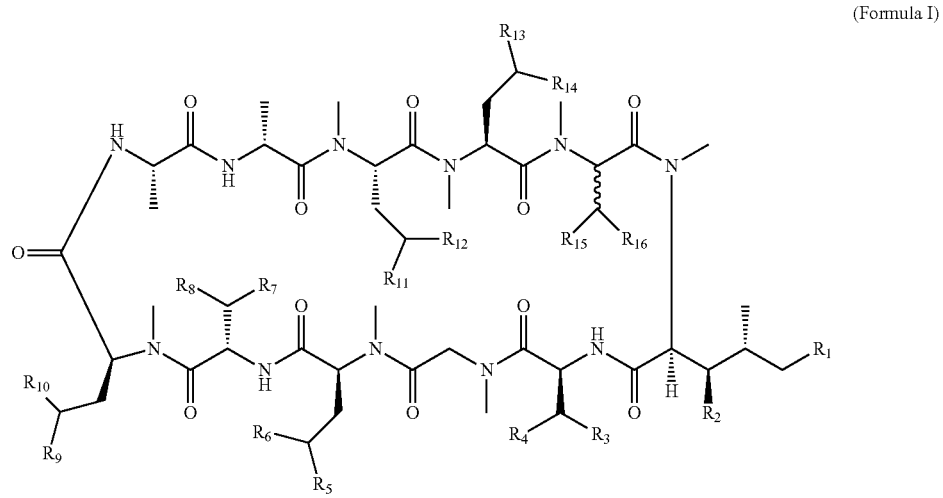

(Formula I)

or a pharmaceutically acceptable salt thereof, wherein:

$R_1$ is —CH=C($R^{1a}$)$_2$ or —CH$_2$C($R^{1a}$)$_3$, wherein each instance of $R^{1a}$ is independently hydrogen, halogen, optionally substituted alkyl, optionally substituted alkenyl, or optionally substituted alkynyl;

$R_2$ is —OR$^{2a}$ or —N(R$^{2a}$)$_2$, wherein each instance of $R^{2a}$ is independently hydrogen or optionally substituted alkyl; and each of $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, and $R_{16}$ is independently hydrogen, halogen, or optionally substituted alkyl.

The term "halo" or "halogen" refers to fluorine (fluoro, —F), chlorine (chloro, —Cl), bromine (bromo, —Br), or iodine (iodo, —I).

The term "alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tert-amyl), and hexyl ($C_6$) (e.g., n-hexyl). Additional examples of alkyl groups include n-heptyl ($C_7$), n-octyl ($C_8$), n-dodecyl ($C_{12}$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-12}$ alkyl (such as unsubstituted $C_{1-6}$ alkyl, e.g., —$CH_3$ (Me)).

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). In certain embodiments, the alkenyl group is an unsubstituted $C_{1-20}$ alkenyl. In certain embodiments, the alkenyl group is a substituted $C_{1-20}$ alkenyl. In an alkenyl group, a C=C double bond for which the stereochemistry is not specified (e.g., —CH=CHCH$_3$ or

)

may be in the (E)- or (Z)-configuration.

The term "alkynyl" refers to a radical of a straight-chain or branched hydrocarbon group having from 1 to 20 carbon atoms and one or more carbon-carbon triple bonds (e.g., 1, 2, 3, or 4 triple bonds) ("$C_1$-20 alkynyl"). In some embodiments, an alkynyl group has 1 to 10 carbon atoms ("$C_{1-10}$ alkynyl"). In some embodiments, an alkynyl group has 1 to 9 carbon atoms ("$C_{1-9}$ alkynyl"). In some embodiments, an alkynyl group has 1 to 8 carbon atoms ("$C_{1-8}$ alkynyl"). In some embodiments, an alkynyl group has 1 to 7 carbon atoms ("$C_{1-7}$ alkynyl"). In some embodiments, an alkynyl group has 1 to 6 carbon atoms ("$C_{1-6}$ alkynyl"). In some embodiments, an alkynyl group has 1 to 5 carbon atoms ("$C_{1-5}$ alkynyl"). In some embodiments, an alkynyl group has 1 to 4 carbon atoms ("$C_{1-4}$ alkynyl"). In some embodiments, an alkynyl group has 1 to 3 carbon atoms ("$C_{1-3}$ alkynyl"). In some embodiments, an alkynyl group has 1 to 2 carbon atoms ("$C_{1-2}$ alkynyl"). In some embodiments, an alkynyl group has 1 carbon atom ("$C_1$ alkynyl"). The one or more carbon-carbon triple bonds can be internal (such as in 2-butynyl) or terminal (such as in 1-butynyl). Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{1-20}$ alkynyl. In certain embodiments, the alkynyl group is a substituted $C_{1-20}$ alkynyl.

The disclosure, in some aspects, relates to methods for inhibiting amyloid synthesis in a subject using sub-therapeutic doses of compounds including NFAT/calcineurin inhibitors. NFAT (nuclear factor of activated T cells) is a transcriptional activator. In its inactive state NFAT resides in the cytoplasm where it is phosphorylated. Increases in intracellular Ca2+ lead to activation of the calmodulin-dependent phosphatase calcineurin (CaN), which subsequently dephosphorylates NFAT permitting its translocation to the nucleus where it promotes gene activation. In some embodiments the NFAT inhibitor may be a calcinuerin inhibitor and/or may be lipid soluble. The NFAT inhibitor may be selected from: cyclosporin, cyclosporin derivatives, tacrolimus derivatives, pyrazoles, pyrazole derivatives, phosphatase inhibitors, S1P receptor modulators, toxins, paracetamol metabolites, fungal phenolic compounds, coronary vasodilators, phenolic adeide, flavanols, thiazole derivatives, pyrazolopyrimidine derivatives, benzothiophene derivatives, rocaglamide derivatives, diaryl triazoles, barbiturates, antipsychotics (penothiazines), serotonin antagonists, salicylic acid derivatives, phenolic compounds derived from propolis or pomegranate, imidazole derivatives, pyridinium derivatives, furanocumarins, alkaloids, triterpenoids, terpenoids, oligonucleotides, peptides, A 285222, endothall, 4-(fluoromethyl)phenylphosphate FMPP, norcantharidin, tyrphostins, okadaic acid, RCP1063, cya/cypa (cyclophilin A), isa247 (voclosporin)/cypa, [dat-sar]3-cya, fk506/fkbp12, ascomyxin/fkbp12, pinecrolimus/FKBP12, 1,5-dibenzoyloxymethyl-norcantharidin, am404, btp1, btp2, dibefurin, dipyridamole, gossypol, kaempferol, lie 120, NCI3, PD 144795, Roc-1, Roc-2, Roc-3, ST 1959 (DLI111-it), thiopental, pentobarbital, thiamylal, secobarbital, trifluoperazine, tropisetron, UR-1505, WIN 53071, caffeic acid phenylethyl ester, KRM-III, YM-53792, punicalagin, imperatorin, quinolone alkaloids compounds, impressic acid, oleanane triterpenoid, gomisin N, CaN457-482-AID, CaN424-521-AID, mFATc2106-121-SPREIT, VIVIT peptide, R11-Vivit, ZIZIT cis-pro, INCA1, INCA6, INCA2, AKAP79330-357, RCAN1, RCAN1-4141-197-exon7, RCAN1-4143-163-CIC peptide, RCAN1-495-118-SP repeat peptide, LxVPc 1 peptide, MCV1, VacA, A238L, and A238200-213.

A calcineurin inhibitor may disrupt the activity of calcineurin directly or indirectly. In some embodiments, the calcineurin inhibitor is cyclosporine A, FK506 (tacrolimus), pimecrolimus, or an immunosuppression cyclosporine analog, such as voclosporin. Cyclosporine A and FK506 are both clinically prescribed as immunosuppressants following organ transplantation.

A calcineurin/NFAT pathway inhibitor, as used herein, is a compound that disrupts the activity of the NFAT pathway. Exemplary calcineurin/NFAT inhibitors include, but are not limited to, peptides such as antibodies small molecule compounds, and other compounds which may disrupt interactions. Calcineurin/NFAT inhibitors also include small molecule inhibitors that directly inhibit one or more components of the calcineurin/NFAT, or other agents that inhibit the binding interaction. In some embodiments the small molecule inhibitors are Cyclosporin or FK506.

The calcineurin/NFAT inhibitory compounds of the invention may exhibit any one or more of the following characteristics: (a) reduces activity of the NFAT pathway; (b) prevents, ameliorates, or treats any aspect of a neurodegenerative disease; (c) reduces synaptic dysfunction; (d) reduces cognitive dysfunction; and (e) reduces amyloid-β peptide (Aβ) accumulation, all when administered at sub-therapeutic doses. One skilled in the art can prepare such inhibitory compounds using the guidance provided herein.

The terms reduce, interfere, inhibit, and suppress refer to a partial or complete decrease in activity levels relative to an activity level typical of the absence of the inhibitor. For instance, the decrease may be by at least 20%, 50%, 70%, 85%, 90%, 100%, 150%, 200%, 300%, or 500%, or by 10-fold, 20-fold, 50-fold, 100-fold, 1000-fold, or 104-fold.

In other embodiments, the calcineurin/NFAT compounds described herein are small molecules, which can have a molecular weight of about any of 100 to 20,000 Daltons, 500 to 15,000 Daltons, or 1000 to 10,000 Daltons. The small molecules can be administered using any means known in the art, including inhalation, intraperitoneally, intravenously, intramuscularly, subcutaneously, intrathecally, intraventricularly, orally, enterally, parenterally, intranasally, or dermally.

In some embodiments the subjects are identified as having or at risk of developing amyloid accumulation based on genotype, whether they are APOE4 positive and successfully treated with sub-therapeutic doses of the compounds described herein. If the subject is APOE4 positive, those subjects are at risk of developing Aβ disorders such as CAA. However, those subjects are also sensitive to treatment with a sub-therapeutic dose of an inhibitor of a calcineurin/NFAT pathway.

It will be appreciated that according to each of the aforementioned aspects, the calcineurin/NFAT inhibitor or pharmaceutically acceptable salt thereof is present, or administered, in amount that is sub-therapeutic as a total daily dose typically effective in immunosuppression based therapies or has been previously proposed for treating CAA and Alzheimer's disease or promoting learning and memory when administered alone. A "sub-therapeutic dose" as used herein refers to a dose that is less than a therapeutic dose required to produce an immunosuppressive effect and is used interchangeably with the term "sub-immunosuppressive dose". A "therapeutic" dose, for example is the amount of compound conventionally used in therapy to produce an immunosuppressive effect. The "sub-therapeutic" amount, for example is an amount of compound that is less than the therapeutic amount or dose for the same indication and the same administration route when it is used alone. For example, a sub-therapeutic amount may an amount less than that defined by the manufacturer as being required for therapy. In some embodiments the sub-therapeutic amount can be for instance less than or equal to 90%, 80%, 70%, 60%, 50%, 40%, 30%, 20% or 10% of the conventional therapeutic dosage (in particular for the same indication and the same administration route). In some embodiments the sub-therapeutic amount is less than or equal to 50% of the conventional therapeutic dosage (in particular for the same indication and the same administration route). An immunosuppressive effect is a threshold level of immune response reduction relative to the absence of an immunosuppressive agent.

In preferred embodiments, the amount of calcineurin/NFAT inhibitor is less than 50% of the daily dose of calcineurin/NFAT inhibitor typically effective in immunosuppression-based therapies or has been previously proposed for treating CAA and Alzheimer's disease or promoting learning and memory when used alone. In particular embodiments, the amount of calcineurin/NFAT inhibitor, such as FK506 and cyclosporin A is less than 40%, 30%, 20%, or 10% of the daily dose of calcineurin/NFAT inhibitors typically effective in immunosuppression based therapies or has been previously proposed for treating CAA and Alzheimer's disease or promoting learning and memory when used alone.

Any of the compounds described herein may be used as salts. As used herein, the term "salt" refers to any and all salts and encompasses pharmaceutically acceptable salts. Salts include ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids, such as hydrochloric acid, hydrobromic acid, phosphoric acid, sulfuric acid, and perchloric acid, or with organic acids, such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, hippurate, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al.

describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

In some embodiments the compound is cyclosporin D or a pharmaceutically acceptable salt thereof:

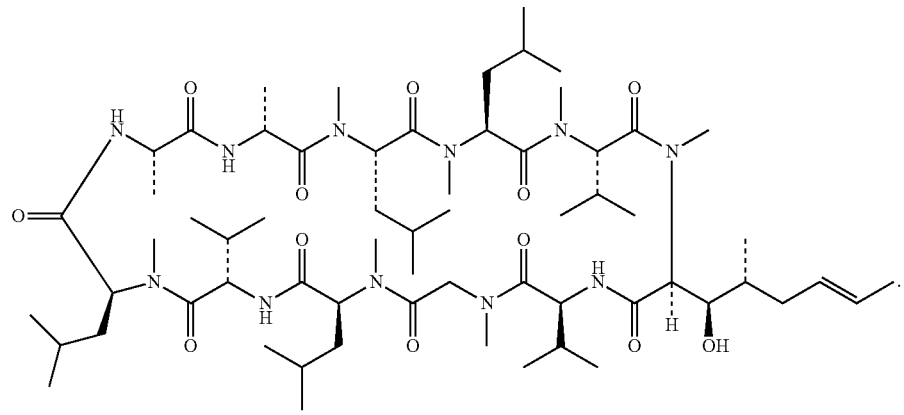 [SMILES: C/C=C/C[C@@H](C)[C@@H](O)[C@H]1C(=O)N[C@@H](C(C)C)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

In other embodiments the compound is cyclosporin H (5-(N-methyl-D-valine)-cyclosporin A) or a pharmaceutically acceptable salt thereof:

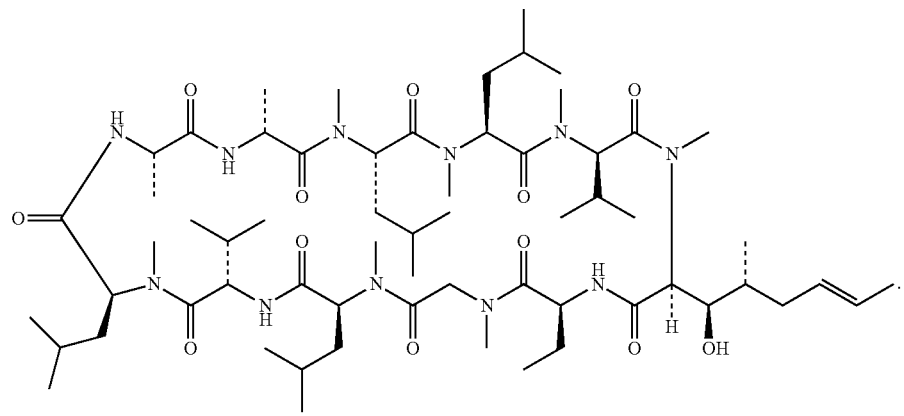 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@H](C(C)C)C(=O)N1C]

The methods disclosed herein are useful for inhibiting amyloid synthesis in a subject.

In some embodiments, the methods are directed to treating or managing neurodegenerative diseases or disorders in which reduction of ApoE in the CNS reduces abnormal amyloid synthesis and/or accumulation. In a non-limiting example, the compounds disclosed herein are administered to a patient diagnosed as having or at risk for developing an amyloid-related neurodegenerative disease or disorder such as Alzheimer's disease, cerebral amyloid angiopathy (CAA), mild cognitive impairment, moderate cognitive impairment, and combinations thereof.

The term "amyloidosis," as used herein, refers to a group of diseases and disorders caused by or associated with amyloid or amyloid-like proteins and includes, but is not limited to, diseases and disorders caused by the presence or activity of amyloid-like proteins in monomeric, fibril, or polymeric state, or any combination of the three, including by amyloid plaques. Such diseases include, but are not limited to, secondary amyloidosis and age-related amyloidosis, such as diseases including, but not limited to, neurological disorders such as Alzheimer's Disease, diseases or conditions characterized by a loss of cognitive memory capacity such as, for example, mild cognitive impairment (MCI), Lewy body dementia, Down's syndrome, hereditary cerebral hemorrhage with amyloidosis (Dutch type), the Guam Parkinson-Demential complex and other diseases which are based on or associated with amyloid-like proteins such as progressive supranuclear palsy, multiple sclerosis, Creutzfeld Jacob disease, Parkinson's disease, HIV-related dementia, ALS (amyotropic lateral sclerosis), inclusion-body myositis, adult onset diabetes, endocrine tumor and senile cardiac amyloidosis, and various eye diseases including macular degeneration, drusen-related optic neuropathy, glaucoma, and cataract due to beta-amyloid deposition.

The subject may have been the subject has been diagnosed with the disease, such as Alzheimer's disease. In some embodiments the subject can be treated following diagnosis, at varying stage of the disease, or as a prophylactic measure in instances where genetic traits, family history, or other factors put the patient at risk for the neurodegenerative disease or disorder. Successful dosage amounts and schedules may be established and monitored by metrics indicative of effective treatment, for example the extent of inhibition, delay, prevention or reduction of symptoms such as cognitive decline, beta-amyloid plaque formation in the brain, and neurodegeneration which are detected following the initiation of treatment.

In some embodiments the subject is determined to have or is at risk of developing amyloid accumulation by identifying the subject as APOE4 positive. A number of genetic factors in early- and late-onset familial Alzheimer's disease have been documented. The ApoE4 allele is strongly associated with late-onset familial and sporadic Alzheimer's disease, with a reported allele frequency of 50%-65% in patients with Alzheimer's disease, which is approximately three times that in the general population and for other neurologic disorders. In addition to Alzheimer's disease, the ApoE4 allele has been implicated in other amyloid-forming disorders, including CAA.

Thus, in some embodiments the methods disclosed herein are useful for treating Alzheimer's disease. The methods of treatment may alleviate the pathological symptoms of Alzheimer's disease, including and not limited to amyloidβ accumulation or aggregation, brain cell aging, and (3) synapse loss. As used herein, the "inhibiting accumulation and/or aggregation" encompasses inhibiting aggregation by suppressing the production or synthesis of amyloid β and/or inhibiting accumulation by degrading already produced amyloidβ.

The deposition of extracellular amyloid plaques in the brain is a hallmark pathologic finding in Alzheimer's disease. These amyloid plaques are primarily composed of Abeta peptides generated by the sequential cleavage of amyloid precursor protein ("APP") via β and γ-secretase activity. Techniques and tools have been developed to visualize the presence of plaques in patients. For example, position emission tomography ("PET") scans using imaging agents, such $^{18}$F-florbetapir, that detect amyloid-beta can be used to detect the presence of amyloid in the brain.

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, such subject or patient is eligible for treatment for amyloidosis. In one embodiment, such eligible subject or patient is one that is experiencing or has experienced one or more signs, symptoms, or other indicators of an amyloid disease or has been diagnosed with an amyloid disease, whether, for example, newly diagnosed, previously diagnosed or at risk for developing amyloid disease such as Alzheimer's disease. Diagnosis of amyloid disease may be made based on clinical history, clinical examination, and established imaging modalities. A "patient" or "subject" herein includes any single human subject eligible for treatment who is experiencing or has experienced one or more signs, symptoms, or other indicators of amyloid disease. Intended to be included as a subject are any subjects involved in clinical research trials, or subjects involved in epidemiological studies, or subjects once used as controls.

The methods of treatment provided herein can be applied to subjects suffering from Alzheimer's disease or other amyloidosis. The subject may, in some embodiments have mild to moderate Alzheimer's disease. In other embodiments the subject may have moderate to severe Alzheimer's disease. The severity of the disease can be assessed using a number of diagnostic criteria known in the art, such as biomarkers. For instance mild Alzheimer's disease or Stage 1 disease may be an asymptomatic cerebral amyloidosis characterized by PET or CSF positive for amyloid β, a Stage 2 disease may show downstream neurodegeneration biomarkers such as tau, FDG-PET, or structural MRI, and Stage 3 disease may present as amyloidosis plus neuronal injury and cognitive/behavioral decline.

In some aspects, the methods provided herein are methods of reducing or slowing decline due to Alzheimer's disease in patients suffering from early, mild, or mild to moderate Alzheimer's disease. In some embodiments, the decline is one or more of: clinical decline, cognitive decline, and functional decline. In some embodiments, the decline is a decline in cognitive capacity or cognitive decline. In some embodiments, the decline comprises a decline in functional capacity or functional decline. Various tests and scales have been developed to measure cognitive capacity (including memory) and/or function. In various embodiments, one or more test is used to measure clinical, functional, or cognitive decline. A standard measurement of cognitive capacity is the Alzheimer's Disease Assessment Scale Cognitive (ADAS-Cog) test, for example, the 12-item ADAS-Cog or ADAS-Cog12, or the 13-item ADAS-Cog or ADAS-Cog-13. Thus, in some embodiments, the reduction or slowing in decline in cognitive capacity (or cognitive decline) in patients being treated with the compounds of the invention is determined using the ADAS-Cog12 test. An increase in ADAS-Cog12 score is indicative of worsening in a patient's condition. In some embodiments, the reduction or slowing in cognitive decline in patients being treated with the compounds of the invention is determined by a Clinical Dementia Rating Scale/Sum of Boxes (CDR-SB) score. In some embodiments, reduction or slowing in functional decline (or decline in functional ability) in patients being treated with the compounds of the invention is determined using the Instrumental Activities of Daily Living (iADL) scale. In some embodiments, decline of one or more types is assessed and one or more of the foregoing tests or scales is used to measure reduction or slowing in decline.

Amyloid-positive subjects or patients may have brain amyloid load consistent with that seen in patients diagnosed with Alzheimer's disease. A subject suffering from mild cognitive impairment or Alzheimer's disease or having preclinical Alzheimer's disease, prodromal Alzheimer's disease, early or mild Alzheimer's disease, are typically subjects with an MMSE score of 20 or above (e.g., 20-30, 20-26, 24-30, 21-26, 22-26, 22-28, 23-26, 24-26, or 25-26) or with a Clinical Dementia Rating-Global Score (CDR-GS) of 0.5 or 1.0, and subjects with a Free and Cued Selective Reminding Test-Immediate Recall (FCSRT-IR) Cueing Index of 0.67 or above and a total free recall score of 27 or greater.

Several Alzheimer's disease-risk genes are expressed in cells that constitute the brain and may directly influence the accumulation and clearance of Aβ. In particular, Apolipoprotein E (APOE) protein is highly expressed in astrocytes and microglia of the brain. In humans, there are three genetic polymorphisms of APOE, ε2, ε3, and ε4. The ε4 isoform of APOE (APOE4) is the most significant known risk factor for CAA and sporadic Alzheimer's disease. In some embodiments, subjects are carriers of at least one ApoE4 allele ("ApoE4 carriers").

Alleviating a neurodegenerative disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a neurodegenerative disease includes initial onset and/or recurrence.

The compound is administered to the brain of the patient, either directly or indirectly by administration to other regions of the body. The compound may be administered directly by intracerebroventricular injection. The compound may be administered indirectly to the brain by administration through any route that delivers a compound to a body of a subject. In some embodiments the compound is administered as an immediate release formulation. In some embodiments the compound is administered as an sustained release formulation.

In some embodiments the subject is treated with another therapeutic agent. In one embodiment, the pharmacological agents that would, in combination with the compounds of the present invention, be most effective in treating or ameliorating one or more symptoms of amyloid disorders include, but are not limited to, Razadyne, Exelon, Aricept, Cognex, and Namenda, Parcopa, Mirapex, Requip, Apokyn, Eldepryl, Zelapar, Azilect, Comtan, Tasmar, Cogentin, Sinemet, Neupro, Symmetrel, Selegiline, Rasagilene, Stalevo, Apokyn, Parlodel, and Artane. In one embodiment, the pharmacological agents that would, in combination with the compounds of the present invention, be most effective in treating or ameliorating one or more symptoms of neurodegenerative disorders include, but are not limited to, Zarontin, Felbatol, Gabitril, Keppra, Lamictal, Lyrica, Neurontin, Dilantin, Topamax, Trileptal, Depakene, Depakote, Zonegran, Valium, Ativan, Klonopin, Fycompa, and Oxtellar XR. In one embodiment, the pharmacological agents that would, in combination with the compounds of the present invention, be most effective in treating or ameliorating one or more symptoms of neurodegenerative disorders include, but are not limited to, Xenazine, Haldol, Clozaril, Klonopin, Valium, Lexapro, Prozac, Sarafem, Zoloft, Lithobid, Depakene, Depakote, and Lamictal. In one embodiment, the pharmacological agents that would, in combination with the compounds of the present invention, be most effective in treating or ameliorating one or more symptoms of neurodegenerative disorders include, but are not limited to, Aricept, Reminyl, Exelon, Namenda, Risperdal, Zyprexa, and selective serotonin reuptake inhibitors (SSRIs). In one embodiment, the SSRIs are selected from the group consisting of Zimelidine, Celexa (citalopram), Lexapro, Luvox, Paxil (paroxetine), Prozac (fluoxetine), and Zoloft (sertraline).

Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. The pharmaceutical compositions to be used in the present methods can comprise pharmaceutically acceptable carriers, excipients, or stabilizers in the form of lyophilized formulations or aqueous solutions. (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™ (polysorbate), PLURONICS™ (poloxamers) or polyethylene glycol (PEG).

In one embodiment, the pharmaceutical formulations include those suitable for oral, parenteral (including subcutaneous, intradermal, intramuscular, intravenous, and intraarticular), inhalation (including fine particle dusts or mists which may be generated by means of various types of metered doses, pressurized aerosols, nebulizers or insufflators), rectal and topical (including dermal, transdermal, transmucosal, buccal, sublingual, and intraocular) administration, although the most suitable route may depend upon, for example, the condition and disorder of the recipient. Pharmaceutically acceptable excipients and salts are further described herein. In some embodiments the pharmaceutically acceptable salt is a hydrochloride.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

In one embodiment, formulations of the present invention that are suitable for oral administration may be presented as discrete units such as capsules, cachets or tablets each containing a predetermined amount of the compound of Formula I or pharmaceutically acceptable salts thereof; as a powder or granules; as a solution or a suspension in an aqueous liquid or a non-aqueous liquid; or as an oil-in-water liquid emulsion or a water-in-oil liquid emulsion. The compound of Formula I or pharmaceutically acceptable salts thereof may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compound of formula I or pharmaceutically acceptable salts thereof can also be delivered through the oral cavity by sublingual and/or buccal administration. Molded tablets, compressed tablets or freeze-dried tablets are exemplary forms which may be used. Exemplary compositions include those formulating the present compounds with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents, thickening agents and P-glycoprotein (P-gp) inhibitors. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremapnor. In one embodiment, compositions for parenteral administration comprise up to 15% Cremaphor and up to 85% alcohol. In one embodiment, compositions for parenteral administration comprise up to 50% Cremaphor and up to 50% alcohol. In one embodiment, compositions for parenteral administration comprise up to 15% Cremaphor and up to 85% ethanol. In one embodiment, compositions for parenteral administration comprise up to 50% Cremaphor and up to 50% ethanol. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. Excipients that can be included are, for instance, non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included.

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin ana glycerine or sucrose and acacia. Exemplary compositions for topical administration include a topical carrier such as Plastibase (mineral oil gelled with polyethylene).

Preferred unit dosage formulations are those containing an effective dose, as disclosed herein. It should be understood that in addition to the ingredients particularly mentioned above, the formulations of this invention may include other agents conventional in the art having regard to the type of formulation in question, for example those suitable for oral administration may include flavoring agents.

The compound of Formula I and/or pharmaceutically acceptable salts thereof are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracistemally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of Formula I and/or pharmaceutically acceptable salts thereof. These compositions exhibit certain biocompatibility features which allow a controlled release of the active substance.

The compound of Formula I and/or pharmaceutically acceptable salts thereof may be delivered by way of a pump or by continuous subcutaneous infusions, for example, using a mini-pump. An intravenous bag solution may also be employed. The key factor in selecting an appropriate dose is the result obtained, as measured by improvements in one or more symptoms of neurodegenerative disorders of interest, or by other criteria for measuring control or prevention of one or more symptoms of neurodegenerative disorders of interest, as are deemed appropriate by the practitioner. In another aspect of the disclosure, compound of Formula (1) and/or pharmaceutically acceptable salts thereof are delivered by way of an implanted pump.

Implantable drug infusion devices are used to provide patients with a constant and long term dosage or infusion of a drug or any other therapeutic agent. Essentially such device may be categorized as either active or passive. The compound of Formula I and/or pharmaceutically acceptable salts thereof may be formulated as a depot preparation. Such a long acting depot formulation can be administered by implantation, for example subcutaneously or intramuscularly; or by intramuscular injection. Thus, for example, the compound of Formula I and/or pharmaceutically acceptable salts thereof can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of the compound of Formula I and/or pharmaceutically acceptable salts thereof may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the course of a week, or during the course of a month.

In some embodiments the daily dose administered to the patient is between 1 and 50 mg and the dose is administered once daily. Therapeutically effective amount of the compound of Formula I and/or pharmaceutically acceptable salts thereof will be dependent on the molecule utilized, the subject being treated, the severity and type of the affliction, and the manner and route of administration. For example, a therapeutically effective amount of the compound of Formula I and/or pharmaceutically acceptable salts thereof may vary from about 0.001 mg/Kg to about 2000 mg/Kg body weight. In one embodiment, a therapeutically effective amount of the compound of Formula I and/or pharmaceutically acceptable salts thereof may vary from about 0.01 mg/Kg to about 1 mg/Kg body weight. In one embodiment, a therapeutically effective amount of the compound of Formula I and/or pharmaceutically acceptable salts thereof may vary from about 0.001 mg/Kg to about 0.9 mg/Kg body weight, about 0.8 mg/Kg body weight, about 0.001 mg/Kg to 0.7 mg/Kg body weight, about 0.001 mg/Kg to 0.6 mg/Kg body weight, about 0.001 mg/Kg to 0.5 mg/Kg body weight, about 0.001 mg/Kg to 0.4 mg/Kg body weight, about 0.001 mg/Kg to 0.3 mg/Kg body weight, about 0.001 mg/Kg to 0.2 mg/Kg body weight, about 0.001 mg/Kg to 0.1 mg/Kg body weight, about 0.001 mg/Kg to 0.09 mg/Kg body weight, about 0.001 mg/Kg to 0.08 mg/Kg body weight, about 0.001 mg/Kg to 0.07 mg/Kg body weight, about 0.001 mg/Kg to 0.06 mg/Kg body weight, about 0.001 mg/Kg to 0.05 mg/Kg body weight, about 0.001 mg/Kg to 0.04 mg/Kg body weight, about 0.001 mg/Kg to 0.03 mg/Kg body weight, about 0.001 mg/Kg to 0.02 mg/Kg body weight. 0.01 mg/Kg body weight, about 0.001 mg/Kg to 0.009 mg/Kg body weight, about 0.001 mg/Kg to 0.008 mg/Kg body weight, about 0.001 mg/Kg to 0.007 mg/Kg body, about 0.001 mg/Kg to 0.006 mg/Kg body, about 0.001 mg/Kg to 0.005 mg/Kg body weight, about 0.001 mg/Kg to 0.004 mg/Kg body weight, about 0.001 mg/Kg to 0.003 mg/Kg body weight, and about 0.001 mg/Kg to about 0.002 mg/Kg body weight. In one embodiment, a therapeutically effective amount of the compound of Formula I and/or pharmaceutically acceptable salts thereof may vary from about 0.001 mg/Kg to about 20 mg/Kg body weight. In one embodiment, a therapeutically effective amount of the compound of Formula I and/or pharmaceutically acceptable salts thereof may vary from about 0.001 mg/Kg to about 10 mg/Kg body weight. In one embodiment, a therapeutically effective amount of the compound of Formula I and/or pharmaceutically acceptable salts thereof may vary from about 0.001 mg/Kg to about 5 mg/Kg body weight. In one embodiment, a therapeutically effective amount of the compound of Formula I and/or pharmaceutically acceptable salts thereof may vary from about 0.001 mg/Kg to about 3 mg/Kg body weight. In one embodiment, a therapeutically effective amount of the compound of Formula I and/or pharmaceutically acceptable salts thereof may vary from 0.001 mg/Kg to about 2 mg/Kg body weight. In one embodiment, a therapeutically effective amount of the compound of Formula I and/or pharmaceutically acceptable salts thereof may vary from about 0.001 mg/Kg to about 30 mg/Kg body weight. In one embodiment, a therapeutically effective amount of the compound of Formula I and/or pharmaceutically acceptable salts thereof may vary from about 0.001 mg/Kg to about 40 mg/Kg body weight. In one embodiment, a therapeutically effective amount of the compound of Formula I and/or pharmaceutically acceptable salts thereof may vary from about 0.001 mg/Kg to about 50 mg/Kg body weight. In one embodiment, a therapeutically effective amount of the compound of Formula I and/or pharmaceutically acceptable salts thereof may vary in a range selected from the group consisting of about 0.001 mg/kg body weight, about 0.002 mg/kg body weight, about 0.003 mg/kg body weight, about 0.004 mg/kg body weight, about 0.005 mg/kg body weight, about 0.006, mg/kg body weight, about 0.007 mg/kg body weight, about 0.008 mg/kg body weight, about 0.009 mg/kg body weight, about 0.010 mg/kg body weight, about 0.011 mg/kg body weight, about 0.012 mg/kg body weight, about 0.013 mg/kg body weight, about 0.014 mg/kg body weight, about 0.015 mg/kg body weight, about 0.016 mg/kg body weight, about 0.017 mg/kg body weight, about 0.018 mg/kg body weight, about 0.019 mg/kg body weight, about 0.20 mg/kg body weight, about 0.030 mg/kg body weight, about 0.040 mg/kg body weight, about 0.050 mg/kg body weight, about 0.060 mg/kg body weight, about 0.070 mg/kg body weight, about 0.080 mg/kg body weight, about 0.090 mg/kg body weight, about 0.010 mg/kg body weight, about 0.02 mg/kg body weight, about 0.03 mg/kg body weight, about 0.04 mg/kg body weight, about 0.05 mg/kg body weight, about 0.06 mg/kg body weight, about 0.07 mg/kg body weight, about 0.08 mg/kg body weight, about 0.09 mg/kg body weight, about 0.10 mg/kg body weight, about 0.2 mg/kg body weight, about 0.3 mg/kg body weight, about 0.4 mg/kg body weight, about 0.5 mg/kg body weight, about 0.6 mg/kg body weight, about 0.7 mg/kg body weight, about 0.8 mg/kg body weight, about 0.9 mg/kg body weight, about 1 mg/kg body weight, about 2 mg/kg body weight, about 3 mg/kg body weight, about 4 mg/kg body weight, about 5 mg/kg body weight, about 6 mg/kg body weight, about 7 mg/kg body weight, about 8 mg/kg body weight, about 9 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, about 20 mg/kg body weight, about 21 mg/kg body weight, 22 mg/kg body weight, 23 mg/kg body weight, 24 mg/kg body weight, 25 mg/Kg body weight, about 50 mg/Kg body weight, about 75 mg/Kg body weight, about 100 mg/Kg body weight, about 125 mg/Kg body weight, about 150 mg/Kg body weight, about 175 mg/Kg body weight, about 200 mg/Kg body weight, about 225 mg/Kg body weight, about 250 mg/Kg body weight, about 275 mg/Kg body weight, about 300 mg/Kg body weight, about 325 mg/Kg body weight, about 350 mg/Kg body weight, about 375 mg/Kg body weight, about 400 mg/Kg body weight, about 425 mg/Kg body weight, about 450 mg/Kg body weight, about 475 mg/Kg body weight, about 500 mg/Kg body weight, about 525 mg/Kg body weight, about 550 mg/Kg body weight, about 575 mg/Kg body weight, about 600 mg/Kg body weight, about 625 mg/Kg body weight, about 650 mg/Kg body weight, about 675 mg/Kg body weight, about 700 mg/Kg body weight, about 725 mg/Kg body weight, about 750 mg/Kg body weight, about 775 mg/Kg body weight, about 800 mg/Kg body weight, about 825 mg/Kg body weight, about 850 mg/Kg body weight, about 875 mg/Kg body weight, about 900 mg/Kg body weight, about 925 mg/Kg body weight, about 950 mg/Kg body weight, about 975 mg/Kg body weight, and about 1000 mg/Kg body weight.

In some embodiments, a therapeutically effective amount of the compound of Formula I and/or pharmaceutically acceptable salts thereof is selected from the group consisting of about 0.01 mg/m$^2$, about 0.02 mg/m$^2$, about 0.03 mg/m$^2$, about 0.04 mg/m$^2$, about 0.05 mg/m$^2$, about 0.06 mg/m$^2$, about 0.07 mg/m$^2$, about 0.08 mg/m$^2$, about 0.09 mg/m$^2$, and about 0.1 mg/m$^2$.

In some embodiments, a therapeutically effective amount of the compound of Formula I and/or pharmaceutically acceptable salts thereof is selected from the group consisting of about 0.1 mg/m$^2$, about 0.2 mg/m$^2$, about 0.3 mg/m$^2$, about 0.4 mg/m$^2$, about 0.5 mg/m$^2$, about 0.6 mg/m$^2$, about 0.7 mg/m$^2$, about 0.8 mg/m$^2$, about 0.9 mg/m$^2$, about 1 mg/m$^2$, about 1.1 mg/m$^2$, about 1.2 mg/m$^2$, about 1.3 mg/m$^2$, about 1.4 mg/m$^2$, about 1.5 mg/m$^2$, about 1.6 mg/m$^2$, about 1.7 mg/m$^2$, about 1.8 mg/m$^2$, about 1.9 mg/m$^2$, about 2 mg/m$^2$, about 2.1 mg/m$^2$, about 2.2 mg/m$^2$, about 2.3 mg/m$^2$, about 2.4 mg/m$^2$, about 2.5 mg/m$^2$, about 2.6 mg/m$^2$, about 2.7 mg/m$^2$, about 2.8 mg/m$^2$, about 2.9 mg/m$^2$, and about 3 mg/m$^2$.

In some embodiments, a therapeutically effective amount of the compound of Formula I and/or pharmaceutically acceptable salts thereof is selected from the group consisting of about 4 mg/m$^2$, about 5 mg/m$^2$, about 6 mg/m$^2$, about 7 mg/m$^2$, about 8 mg/m$^2$, about 9 mg/m$^2$, about 10 mg/m$^2$, about 11 mg/m$^2$, about 12 mg/m$^2$, about 13 mg/m$^2$, about 14 mg/m$^2$, about 15 mg/m$^2$, about 16 mg/m$^2$, about 17 mg/m$^2$, about 18 mg/m$^2$, about 19 mg/m$^2$, about 20 mg/m$^2$, about 21 mg/m$^2$, about 22 mg/m$^2$, about 23 mg/m$^2$, about 24 mg/m$^2$, and about 25 mg/m$^2$.

The practice of the present invention will employ, unless otherwise indicated, conventional techniques of molecular biology (including recombinant techniques), microbiology, cell biology, biochemistry and immunology, which are within the skill of the art.

EXAMPLES

In order that the invention described herein may be more fully understood, the following examples are set forth. The examples described in this application are offered to illustrate the methods, compositions, and systems provided herein and are not to be construed in any way as limiting their scope.

The inventors have previously demonstrated that APOE4 increases Aβ accumulation in an in vitro brain (iBBB)

(WO2020/154374). It was found that homozygous ApoE4/4 (E4/4) iBBB exhibited significantly more amyloid accumulation than a homozygous ApoE3/3 (E3/3) genotype. Additionally, iBBBs generated from different heterozygous ApoE3/4 (E3/4) individuals exhibited significantly more amyloid accumulation than iBBBs generated from ε3/3 individuals. The spatial distribution of the increased amyloid accumulation in the APOE4 iBBB was also determined. Significantly more amyloid signal was found on and surrounding BEC vessels of the APOE4 iBBBs compared to APOE3/3 iBBBs further demonstrating that the iBBB can model aspects of amyloid accumulation observed in CAA and AD and a common genetic predisposition to these pathologies.

It was also determined that pericytes are required for the observed increased A3 deposition in the iBBB. In fact replacing E4/4 pericytes with pericytes derived from a different E3/3 individual resulted in a significant reduction in iBBB amyloid deposition regardless of the BEC's or astrocytes' genotype. In determining the mechanism, it was revealed that E4/4 pericyte conditioned media was sufficient to increase amyloid accumulation of the E3/3 iBBB, demonstrating that expression of APOE4 in pericytes promotes increased Aβ deposition in the iBBB via an unknown soluble factor.

Next it was shown that APOE and Calcineurin signaling are up-regulated in APOE4 pericytes. It was determined the dysregulation of the calcineurin pathway in E4/4 pericytes contributes to up-regulated APOE expression, and that inhibiting calcineurin signaling using well-established CaN inhibitors cyclosporine A (CsA), FK506, and INCA6 was effective. Specifically, it was observed that chemical inhibition of CaN in E4 pericytes leads to a reduction in both APOE gene expression and APOE protein. The increased amyloid deposition due to E4/4 pericyte conditioned media is likely due to increased soluble APOE. It was shown that both CsA and FK506 reduced APOE protein abundance and accumulation of Aβ in APOE4KI cortical slice cultures. Thus, the results demonstrated that dysregulation of CaN/NFAT signaling in APOE4 pericytes leads to increased amyloid accumulation through up-regulation of APOE expression in human pericytes, and that this phenotype is ameliorated through pharmacological inhibition of CaN signaling. These results also demonstrated that CaN/NFAT inhibition can reduce pericyte APOE levels and vascular amyloid in vivo.

Example 1: Sub-Immunosuppressive Doses of FK506 Reduce CAA Pathology in APOE4 AD Mouse Models As described above, it was established that increased APOE expression in pericytes mediates APOE4 predisposition to CAA and AD. It was found that treating APOE4 knock-in AD mice with calcineurin/NFAT inhibitors significantly reduced APOE expression in pericytes and vascular amyloid pathology demonstrating that this can be an effective therapeutic strategy. To further therapeutically develop calcineurin inhibitors as a treatment for CAA pathology the in vivo efficacy and toxicity of two FDA-approved calcineurin inhibitors FK506 and Cyclosporine A were compared. It was found that FK506 at 10 mg/kg once a day significantly reduced CAA pathology in 6 month-old APOE4/5×FAD mice and exhibited less toxicity when compared to cyclosporine treated mice. Because FK506 exhibited less toxicity it was selected for further analysis. FK506 has been previously administered as an immunosuppressant following organ transplant. Suppression of the immune system increases the risk of infection and cancer and thus has a concerning toxicity level.

Figure 3:
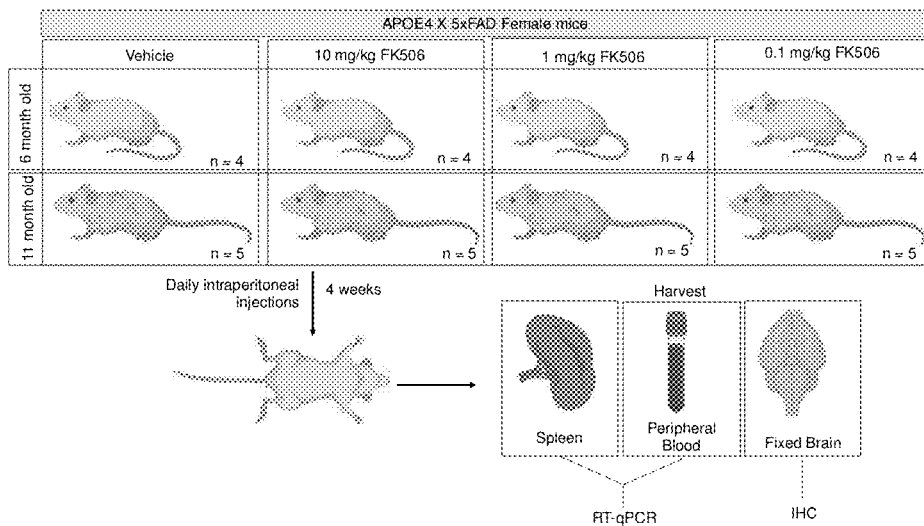
FIG. 3. Experimental setup to determine whether a sub-immunosuppressive dose of FK506 can reduce CAA pathology in APOE4/5xFAD mice.

Sub-immunosuppressive dose of FK506 may have reduced toxicity and increased safety, but prior to the invention it was not clear that such doses would be effective. Therefore, we sought to determine whether a sub-immunosuppressive dose of FK506 could effectively reduce CAA pathology in APOE4 mice. To test this, we treated two cohorts of mice at 6 months of age or 11 months of age with 0, 0.1, 1.0, and 10 mg/kg of FK506 for one month via intraperitoneal injection. After 1 month of treatment, the spleen and peripheral blood were harvested to assess immunosuppression and the brain was fixed and analyzed via immunohistochemistry for CAA pathology (FIG. 3).

Figure 4:
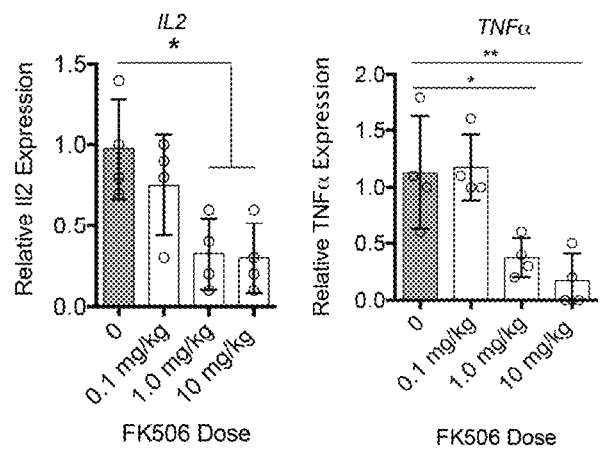
FIG. 4. Low dose (0.1 mg/kg) of FK506 does not reduce expression of immune genes IL2 and TNFa, suggesting that it is a sub-immunosuppressive dose.

Immunosuppressive effects of FK506 have not been shown to be useful previously, it was surprisingly discovered herein that sub therapeutic doses have a significant impact on CAA pathology. Different doses were examined and the expression IL2 and TNFα two common immune response genes in the spleen and peripheral blood were quantified. This revealed that a daily dose 0.1 mg/kg of FK506 does not significantly reduce IL2 or TNFα expression (FIG. 4). In contrast, two higher doses of FK506 (1 mg/kg and 10 mg/kg) significantly reduced both IL2 and TNFα expression compared to control treated mice (FIG. 4). This demonstrates that daily 0.1 mg/kg of FK506 is likely a sub-immunosuppressive dose.

Figures 5A, 5B, 5C:
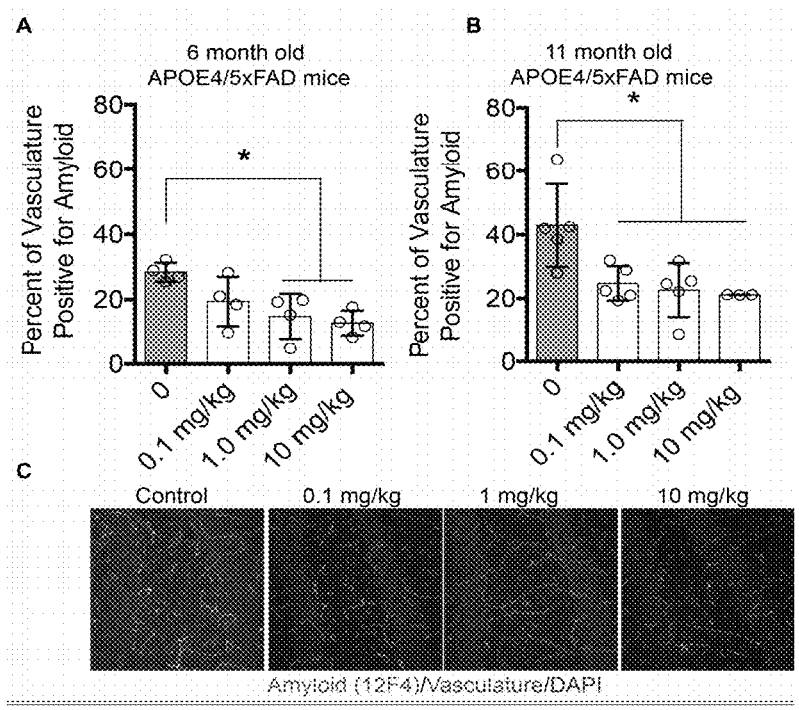
FIGS. 5A-5C. Sub-immunosuppressive FK506 reduces CAA pathology in APOE4/5xFAD mice. 5A) 6 month old 5B) 11 month old mice treated with FK506 at different doses. 5C) Representative images of hippocampal vasculature (1y6e) stained for amyloid (12F4) FIG. 6. Cartoon depicting experimental design for testing cognitive response to low doses of FK506 in APOE4/5xFAD mice.
Figure 6:
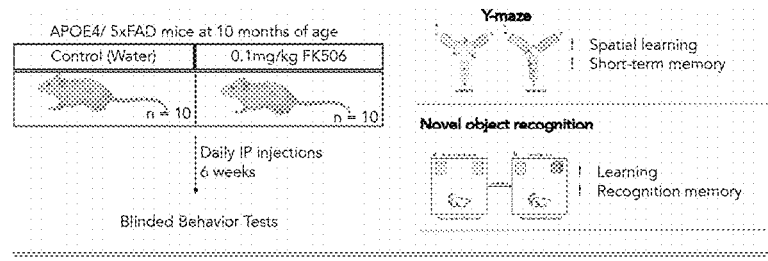
Figure 7:
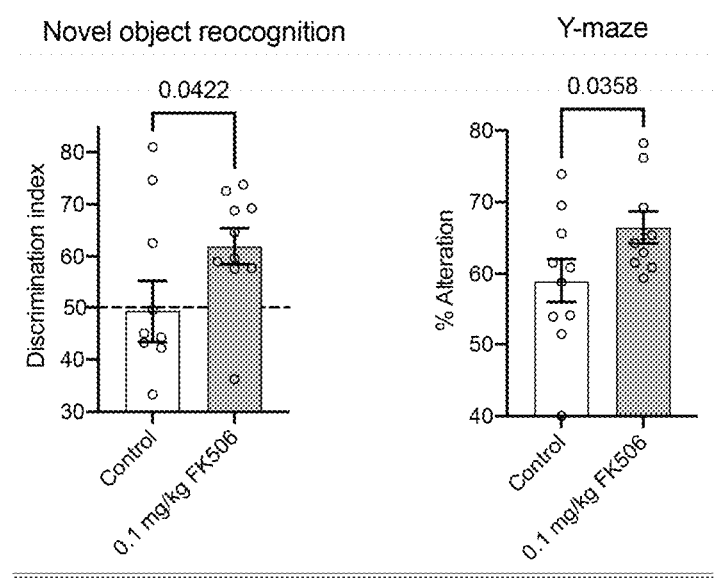
FIG. 7. Low doses of FK506 improve behavior assessments of learning and memory in the APOE4/5xFAD mouse model of AD.

It was next assessed whether sub-immunosuppressive dose of FK506 could reduce CAA pathology. It was found that in 6 month old mice 0.1 mg/kg marginally reduced vascular amyloid accumulation, but due to the limited number of mice tested was not significant. The 11-month-old cohort exhibited significantly more vascular amyloid accumulation. 0.1 mg/kg of FK506. In these mice 0.1 mg/kg FK506 significantly reduced vascular amyloid accumulation (FIG. 5.). This demonstrates that a sub-immunosuppressive dose of FK506 can reduce CAA pathology potentially reducing AD progression.

Example 2: Sub-Immunosuppressive Doses of FK506 Improve Learning and Memory in APOE4 AD Mouse Models It has been shown, quite surprisingly, that sub-immunosuppressive doses of FK506 could reduce CAA pathology in APOE4 AD mice. The effects of sub-immunosuppressive doses of FK506 were next examined for effect on behaviors associated with learning and memory. APOE4/4 knock-in/5×FAD mice were treated via daily intraperitoneal injection of either water or 0.1 mg/kg FK506 for 6 weeks. Mice were then subjected to a battery of behavioral test to assess their response to drug treatment. First mice were tested using the novel object recognition test, which examines the ability to remember previous encounters with objects and distinguish them from unfamiliar objects tasks which require both learning and memory recall. Control mice treated with water had a discrimination index of approximately 50% which was statistically similar to random chance. This suggest that control mice could not distinguish between familiar and unfamiliar objects. In contrast, mice treated with FK506 showed significant improvement preferring unfamiliar objects over familiar. This suggests that mice treated sub-therapeutic with low doses of FK506 had improved object discrimination and memory recall. We next test working spatial memory using the Y-maze. Similar to the novel object recognition test the Y-maze examines the ability to discriminate between familiar and unfamiliar space based on spatial cues. In the Y-maze, control mice again showed impaired spatial memory. In contrast, mice treated with FK506 showed significantly improved spatial recognition indicated by increased arm alterations. These findings suggest that low doses (sub-therapeutic or sub-immunosuppressive) of FK506 improve learning and memory, for instance, in APOE4 AD mouse models.

Example 3: Identification of Non-Immunosuppressant Compounds for Treating Cerebral Amyloid Angiopathy and Alzheimer's Disease FK506 and cyclosporin A can reduce the expression of APOE in human pericytes and brain cells and reverse or prevent cerebrovascular pathologies associated with Alzheimer's Disease such as cerebral amyloid angiopathy. Both cyclosporine A and FK506 have immunosuppressant activity. When analog compounds were screened it was expected that compounds having immuosuppressant activity would be most effective. In contrast, screening revealed that cyclosporin D and cyclosporin H are significantly more potent with faster kinetics and able to reduce APOE expression at lower doses. Results showing APOE expression after APOE4 pericytes were treated with Cyclosporin analogs for two weeks are depicted in FIG. 1. Following treatment with Cyclosporin A, FK506, Cyclosporin D, Cyclosporin H, APOE expression was measured by qRT-PCR in APOE4/4 pericytes (see FIGS. 2A-2D). This suggests these chemicals may be valuable for the treatment of cerebral amyloid angiopathy and Alzheimer's Disease.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for inhibiting amyloid synthesis in a subject, comprising administering to the subject a non-immunosuppressant cyclosporin and/or a pharmaceutically acceptable salt thereof in an effective amount to inhibit amyloid synthesis in the subject, wherein the non-immunosuppressant cyclosporin is cyclosporin D

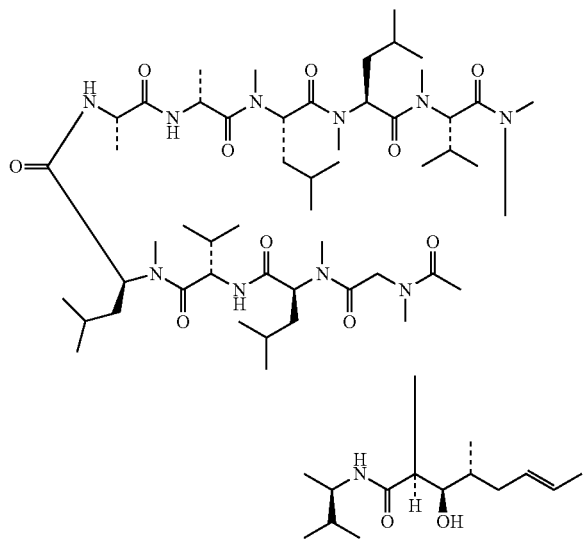

(cyclosporin D); or
wherein the non-immunosuppressant cyclosporin is cyclosporin H (5-(N-methyl-D-valine)-cyclosporin A)

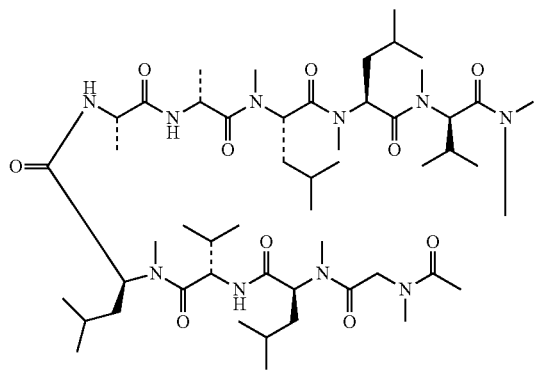

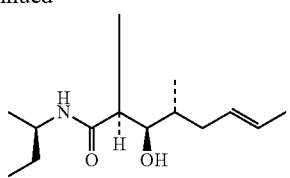

(cyclosporin H); and
wherein the daily dose administered to the subject is a dose of between 1 and 50 mg.

2. The method of claim 1, wherein the subject has Alzheimer's disease.

3. The method of claim 1, wherein the subject has cerebral amyloid angiopathy (CAA).

4. The method of claim 1, wherein the subject has been diagnosed with Alzheimer's disease.

5. The method of claim 1, further comprising determining whether the subject has or is at risk of developing amyloid accumulation by identifying the subject as APOE4 positive.

6. The method of claim 1, wherein the pharmaceutically acceptable salt is a hydrochloride.

7. The method of claim 2, wherein the Alzheimer's disease is mild to moderate Alzheimer's disease.

8. The method of claim 2, wherein the Alzheimer's disease is moderate to severe Alzheimer's disease.

9. The method of claim 1, further comprising administering another therapeutic agent.

10. The method of claim 9, wherein the therapeutic agent is a calcineurin/NFAT inhibitor.

11. The method of claim 1, wherein the subject has a defect in learning and memory.

\* \* \* \* \*